US008671602B2

(12) United States Patent
Seidl

(10) Patent No.: US 8,671,602 B2
(45) Date of Patent: Mar. 18, 2014

(54) IDENTIFICATION LABEL FOR A CYLINDRICAL VESSEL, AND CYLINDRICAL VESSEL

(75) Inventor: Peter Seidl, Munich (DE)

(73) Assignee: Schreiner Group GmbH & Co. KG, Oberschleissheim (DE)

( * ) Notice: Subject to any disclaimer, the term of this patent is extended or adjusted under 35 U.S.C. 154(b) by 124 days.

(21) Appl. No.: 13/453,296

(22) Filed: Apr. 23, 2012

(65) Prior Publication Data

US 2012/0279103 A1 Nov. 8, 2012

(30) Foreign Application Priority Data

May 2, 2011 (DE) .................... 20 2011 100 113 U

(51) Int. Cl.
*B42D 15/00* (2006.01)
*G09F 3/00* (2006.01)

(52) U.S. Cl.
USPC .................... 40/630; 40/638; 40/310; 283/81

(58) Field of Classification Search
USPC ............. 40/310–313, 630, 638, 306; 283/81, 283/900; 206/534, 807
See application file for complete search history.

(56) References Cited

U.S. PATENT DOCUMENTS 4,763,930 A * 8/1988 Matney .......................... 283/81
4,884,827 A * 12/1989 Kelley .......................... 283/81
4,921,277 A 5/1990 McDonough
5,165,725 A * 11/1992 Gollon .......................... 283/81
6,860,513 B2 * 3/2005 Kaufman ........................ 283/81
7,534,477 B1 * 5/2009 Waggoner et al. ........... 428/40.1
7,794,809 B2 * 9/2010 Plummer .................... 428/40.1

FOREIGN PATENT DOCUMENTS

DE 91 15 228 5/1992
DE 602 21 589 4/2008
DE 20 2010 011 326 2/2011

* cited by examiner

*Primary Examiner* — Casandra Davis
(74) *Attorney, Agent, or Firm* — Collard & Roe, P.C.

(57) ABSTRACT

An identification label for a cylindrical vessel has a first label portion with an underside coated with adhesive, an opaque second label portion with a non-adhesive underside and a transparent third label portion with an underside coated with adhesive. The transition from a first outside edge of the first label portion and a second outside edge of the third label portion has a rounded line profile.

11 Claims, 2 Drawing Sheets

IDENTIFICATION LABEL FOR A CYLINDRICAL VESSEL, AND CYLINDRICAL VESSEL

CROSS REFERENCE TO RELATED APPLICATIONS

Applicant claims priority under 35 U.S.C. §119 of German Application No. 20 2011 100 113.3 filed May 2, 2011, the disclosure of which is incorporated by reference.

BACKGROUND OF THE INVENTION

1. Field of the Invention

The present invention relates to an identification label for a cylindrical vessel, as well as to a cylindrical vessel that is provided with an identification label. In particular, the invention relates to an identification label for thin injection syringes, and to injection syringes that are identified with such a label.

2. The Prior Art

In the pharmaceutical and medical field, it is very important to be able to easily identify individual products, such as medications, blood samples or similar, for example. Since these products as a rule concern a very specific person and mix-ups are associated with great risks, it must be ensured from the beginning that each product is clearly identified at every moment. Potential mix-ups and sometimes life-threatening risks must be avoided, even in stressful situations.

For the safety of the identified pharmaceutical and medical products, it is also very important that the identification be securely joined with the product during the entire lifetime and, for example, that a glued-on label not be easily detached.

Moreover, the identification should always be very legible. The identification should not be adversely affected by any kind of environmental or similar influences such that the inscription would become illegible or that mix-ups could occur.

Furthermore, modern identification should also permit rapid and efficient processing. This means that the identification can be generated by machine. Different methods of automated printing are suitable for this purpose. Already during manufacture, for example, a corresponding label may even be printed simultaneously with an identification. However, even a completely individual separate inscription, mad for example by ink-jet or thermal-transfer printing, is possible. In particular, during subsequent inscription with an ink-jet printer, the inscription may be damaged very easily by environmental influences, such as humidity. Therefore, suitable protection is necessary in these cases.

Modern production and processing techniques very often also require automated recognition of already identified products. Besides the optical character recognition (OCR), reading devices for bar codes or data matrix codes are also used very frequently for this purpose. For these optical recognition methods, however, it is necessary for the identification area of a product to be passed as flatly as possible in front of the recognition device. Especially for cylindrical vessels with a narrow radius, such as thin injection syringes, for example, optical recognition cannot be assured as a rule. The identification in these cases is usually extended over more than half the circumference, so that automated recognition is not possible at all or only with considerable complexity.

SUMMARY OF THE INVENTION

It is therefore an object of the present invention to provide an identification label that permits a reliable automated recognition even for cylindrical vessels with a narrow radius and at the same time remains securely joined with the vessel.

This is accomplished by an identification label for a cylindrical vessel that comprises a first, a second and a third label portion. The first label portion comprises an underside coated at least partially with adhesive. The second label portion is at least partially opaque and comprises an at least partially non-adhesive underside. The third label portion is at least partially transparent and comprises an underside coated at least partially with adhesive. The transition from a first outside edge of the first label portion to a second outside edge of the third label portion has a rounded edge profile.

It is an object of this invention that the identification label possesses, by virtue of the non-adhesive underside of the second label portion, a label part that is not completely joined with the product to be identified but instead projects from the cylinder of the product. Thus an approximately plane, straight banner can be formed. This banner may be sensed and read substantially more easily by a person or a machine than a label completely glued onto the curved shell surface.

On the other hand, sharp-edged angles at the places of the label particularly exposed to tearing are avoided, and these corners are replaced by a rounded line profile of the outer punch lines. Thus, the risk of a tearing of the label film is significantly minimized. In particular, the part of the identification label that projects from the labeled product will not be easily detached and thus the identification will not be lost.

Preferably, the underside of the second label portion is coated with adhesive, and the effect of the adhesive is at least partly neutralized here. Thus, for the manufacture of the identification label, the entire label may be coated with adhesive over the entire surface at first. Thereafter only the partial area at which no adhesive effect is desired will be neutralized by applications of a glue killer.

Preferably, the upper side of the second label portion is coated at least partially with an opaque paint. As a result, the applied information for the identification is clearly legible and visible with good contrast.

The first, the second and the third label portions are preferably manufactured from the same film or film composite. A film from a transparent plastic, for example polyester, is advantageous for this. The individual label portions will be manufactured by suitable punching in a simple production method.

Preferably, the second label portion comprises an area with imprinted information. In addition, the information is preferably imprinted in the form of a machine-readable code. Thus, the identification of a product may be easily sensed even in an automated reading process.

In a preferred embodiment, an identification label according to the invention is applied onto a cylindrical vessel so that the first outside edge of the first label portion runs parallel to the cylindrical axis of the vessel. In this way a reliable and highly legible identification of such a vessel is obtained.

Preferably the identification label is applied onto the vessel so that the third label portion at least partially overlaps the second label portion.

Thus, the identification on the second label portion is protected from damage and contamination by the third portion lying above it.

Preferably, the second label portion and the third label portion form a banner, which projects from the cylindrical vessel. The identification can be sensed particularly well automatically by virtue of this projection.

In a preferred embodiment, the cylindrical vessel is a syringe body of an injection syringe. The problems of reliable identification with automatic sensing are particularly great for thin syringes.

BRIEF DESCRIPTION OF THE DRAWINGS

Other objects and features of the present invention will become apparent from the following detailed description considered in connection with the accompanying drawings. It is to be understood, however, that the drawings are designed as an illustration only and not as a definition of the limits of the invention.

In the drawings, wherein similar reference characters denote similar elements throughout the several views.

DETAILED DESCRIPTION OF THE PREFERRED EMBODIMENT

Figure 1:
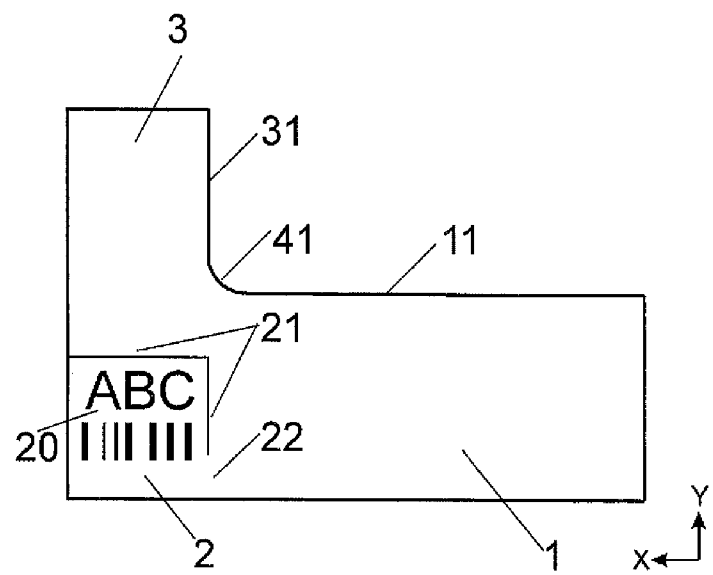
FIG. 1 shows a schematic diagram of a top view of an inventive identification label according to the invention.

Referring now in detail to the drawings, FIG. 1 shows a top view of an identification label according to the invention. The label comprises a first portion 1, which substantially serves for fastening the label to a product to be identified. First portion 1 usually has an approximately rectangular shape, wherein two outside edges run parallel to the axes X and Y respectively in FIG. 1.

The extent in direction Y is then usually somewhat greater than the circumference of the cylinder to be identified. However, this is not an absolute prerequisite for the function of the identification label. An extent of first portion 1 in the Y direction of less than the circumference of the vessel to be labeled is also possible, as long as adequate fastening of the label to the vessel is then assured.

Furthermore, the label comprises a second portion 2, on which an identification 20 of the product is applied. Second portion 2 is adjoined in X direction to first portion 1 and is separated by punch lines 21 from first portion 1 and a third portion 3 described in the following and is joined to first portion 1 only at a non-punched area 22.

Further, the label comprises a transparent third portion 3, which is adjoined in the Y direction to second portion 2. After application of the identification label, third portion 3 comes to lie over second label portion 2 and thus protects the applied identification 20 of second label portion 2 from damage or contamination.

Figure 2:
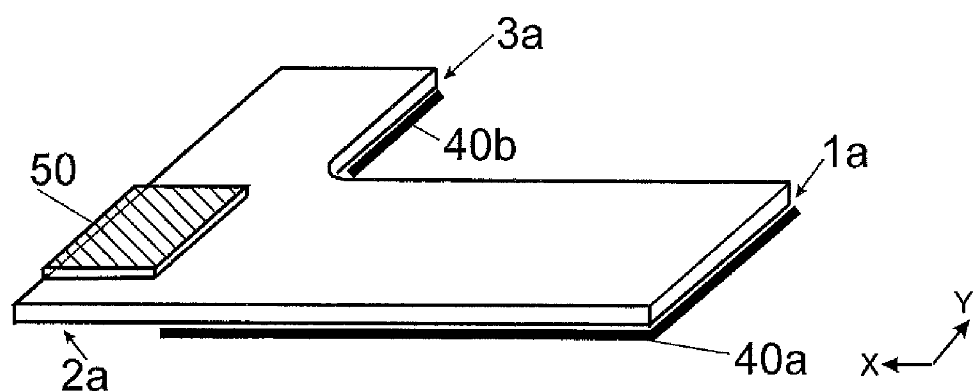
FIG. 2 shows a schematic diagram of a label according to the invention in an oblique view.

Preferably the entire identification label is manufactured from a full-area transparent plastic film. In order to obtain partial opacity of the label, the identification label or the plastic film may be coated partly with a covering, opaque paint 50. This is illustrated in FIG. 2 for the area of second label portion 2. In particular, paints that form a high contrast with an identification 20 to be applied later are suitable for this. If identification 20 is applied in a dark paint, for example, a light, preferably white paint is advantageous for covering paint 50.

At the same time, covering paint 50 may also serve as a primer, which favors or first enables subsequent inscription of the corresponding area. Such priming is of great advantage in particular for thermal-transfer or ink-jet printing. Alternatively, however, it is also possible to apply a further priming coat on paint 50 in a separate production step.

In this case, the application of covering paint 50 and if appropriate also an additional priming coat may take place, for example, in a printing method. Thus the desired areas may be coated very precisely.

The fastening of the identification label to an injection syringe or another cylindrical vessel takes place by means of first label portion 1. In addition, an adhesive 40*a* is disposed on the underside 1*a* of this label portion. Thus the identification label may be glued in a simple manner onto the cylindrical outside face of the product to be identified.

Depending on the special application situation, it may be advantageous that first label portion 1 is made transparent completely or at least in partial areas. Thus this part does not conceal the labeled vessel. A user may even continue to see through the label and thus check the contents of the vessel visually. If the vessel is an injection syringe, for example, the scale of the injection syringe also continues to be visible with a transparent first label portion 1.

Alternatively, first label portion 1 may also be made opaque. Thus this partial area also may be printed with information that may be readily perceived on an opaque, for example white, background.

For gluing the label, the label is preferably laid on with one outside edge parallel to the cylinder axis of the cylindrical vessel. Then the identification label is wrapped around the vessel along the shell surface.

Once the label has completely encircled the circumference of the shell surface in this operation, third label portion 3 comes to lie above second label portion 2. The underside 3*a* of third label portion 3 is also provided with an adhesive 40*b*, so that a firm bond is produced between second label portion 2 and third label portion 3.

The adhesive coating 40*b* of third label portion 3 can then be carried out in the same way as already described for first label portion 1.

Since third label portion 3 is transparent, the identifications 20 of second label portion 2 remain visible despite the protection by third label portion 3. Third label portion 3 therefore serves as protective laminate.

Second label portion 2 is made at least partially non-adhesive on its underside. This may be achieved either by the fact that the underside of the identification label was coated with adhesive only in the area of the first and third label portions. Alternatively, the identification label may be completely coated with adhesive on the underside, after which the adhesive strength of the adhesive is neutralized by a glue killer in the area of second label portion 2. A glue killer is a substance that neutralizes or at least weakens the adhesive strength of the applied adhesive.

Figure 3:
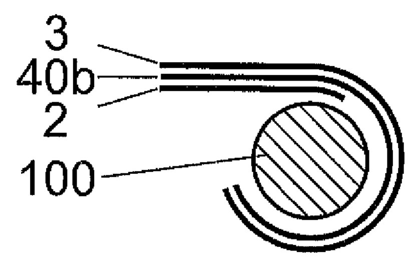
FIG. 3 shows a schematic diagram of a labeled cylindrical vessel in a cross-sectional view.

As illustrated in FIG. 3, the non-adhesive underside of second label portion 2 causes second identification portion 2 to project from the shell surface of the cylindrical vessel 100 and to run approximately straight or to project only with minimum curvature after application of the identification label on the cylindrical shell surface. A portion of the identification label projecting in this way may then be sensed very simply both by a person and also by a suitable automatic reading device, without having to move the identified product to and fro.

Graphic characters, such as letters and numerals printed in a normal typeface, for example, may then be used as identification 20 on the upper side of the second label portion 2. Furthermore, very specially imprinted one- or two-dimensional code sequences, such as a bar code or a data matrix code, for example, are also suitable for automatic sensing.

On the one hand, appropriate printing for entire batches scheduled to receive a common identification may then be carried out already during the process of manufacture of the identification labels. On the other hand, the identification labels may be provided with an individual identification in a subsequent process, so that each identification label represents a unique item in itself. As already pointed out, inscription by means of ink-jet printer or thermal-transfer printer is quite particularly suitable for this individual identification of the individual labels. Even manual inscription by a person by means of a pen is likewise conceivable.

Since it is precisely individual inscriptions that as a rule are made in a method in which the inscription could be very easily damaged or even manipulated, it is particularly advantageous if the identification is simultaneously sealed and thus protected with third label portion 3 during application of the label on the cylindrical product.

As a basis material for the identification label described above, a transparent plastic film, for example of polyester, is particularly suitable. However, even other suitable transparent plastic films are also possible. Preferably, films with a thickness of approximately 38 micrometers are used.

As a rule, identification labels of these materials have relatively good tearing strength, i.e. an undamaged label has good resistance to an incipient tear. However, if the label has already suffered damage and is torn at one place, this tear may propagate very rapidly through the entire label structure.

In a label structure, not illustrated, with a projecting element, the danger exists that the projecting identification element could be torn off. Particularly at risk in the structure described above is then the corner, not illustrated, at which the outside edge 11 of the first label portion 1 and the outside edge 31 of the third label portion 3 meet. The vertex of the right angle between the two outside edges 11 and 31 may very easily suffer slight damage equivalent to a minimum tear during punching during the production process. Thus the projecting label part may tear off very easily starting from this place.

In order to counteract this initial tear formation, the corner 41 in the identification label according to the invention is configured as a circular segment between the two edges 11 and 31. Preferably the circular segment has a radius of 1 millimeter or more. Thus, no pronounced angle with a sharp vertex but instead a gentle transition is formed at the transition between the edges 11 and 31. As a result, the future identification portion becomes considerably more resistant to tearing. In this way, the danger of tearing off of the identification portion may be quite considerably reduced.

Figure 4:
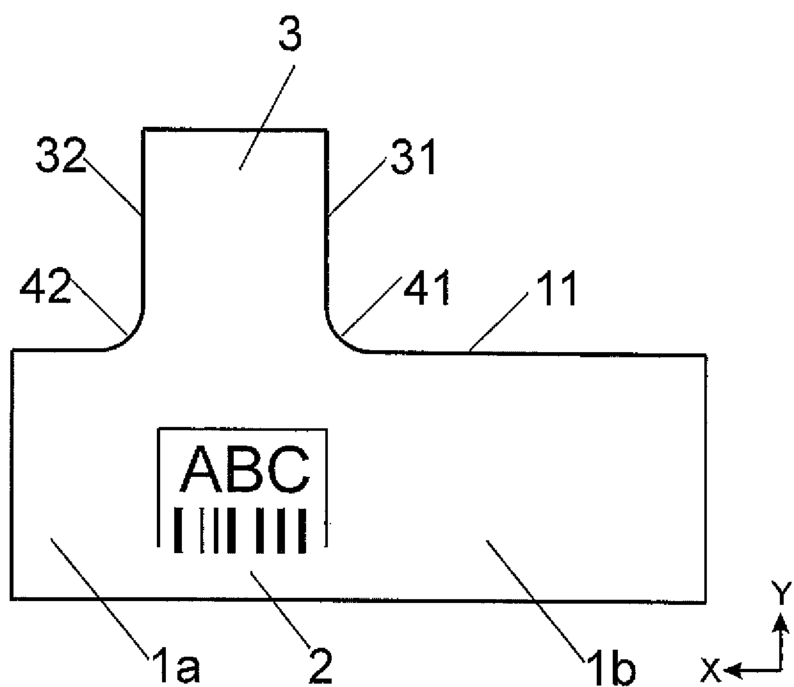
FIG. 4 shows a schematic diagram of a top view of an alternative embodiment of an identification label according to the invention.

FIG. 4 shows an alternative embodiment of the label according to the invention. In this case, the second and third label portions 2 and 3 are not disposed at the border of the identification label but instead lie in a middle region of the identification label. In this case, the first label portion 1*a* and 1*b* is divided into two parts located respectively left and right of the label portions 2 and 3.

In other words, in X-direction of the running axis, part 1*a* of the first label portion is arranged first and is adjoined first by the second label portion 2 and finally by part 1*b* of the first label portion. Portion 2 is therefore surrounded in X direction by the portions 1*a* and 1*b*. As in FIG. 1, the course of the Y-direction is also orthogonal to the X-direction in this case. Here also the third portion 3 is adjoined to the second label portion 2 along the Y-direction.

If such an identification label is applied on a cylindrical vessel, the projecting banner with the identification is located approximately at the middle of the vessel, which is of advantage for certain application cases.

To increase the protection against inadvertent tearing off of the identification banner, the two transitions 41 and 42 from the two edges 31 and 32 of the third label portion to the two parts 1*a* and 1*b* of the first label portion are configured as circular segments in this case.

In summary, with the label structure according to the invention, an identification label for syringes and other cylindrical products with narrow radii is obtained, wherein an identification portion projects relatively straight, so that it can be read relatively easily manually and automatically. The identification may then be achieved with a commercial method even independently of the production of the actual identification label. After application of the label on the cylindrical body, the inscription is protected from contamination, damage or manipulation by sealing with a transparent laminate. The tearing strength of the identification label is significantly increased by avoiding an angle with a sharp vertex in the transition region 41 between the outside edge 11 of the first label portion and the outside edge 31 of the third label portion.

Accordingly, while only a few embodiments of the present invention have been shown and described, it is obvious that many changes and modifications may be made thereunto without departing from the spirit and scope of the invention.

What is claimed is:

1. An identification label for a cylindrical vessel, comprising:

a first label portion with an underside coated with adhesive;

an opaque second label portion with a non-adhesive underside; and a transparent third label portion with an underside coated with adhesive;

wherein a transition from a first outside edge of the first label portion and a second outside edge of the third label portion has a rounded line profile.

2. The identification label according to claim 1, wherein the underside of the second label portion is coated with adhesive and the adhesive is neutralized.

3. The identification label according to claim 1, wherein an upper side of the second label portion is coated with an opaque paint.

4. The identification label according to claim 1, wherein the first label portion, the second label portion and the third label portion are manufactured from a common film.

5. The identification label according to claim 4, wherein the common film is manufactured from a transparent plastic.

6. The identification label according to claim 1, wherein the second label portion comprises an area with imprinted information.

7. The identification label according to claim 6, wherein the information is imprinted in the form of a machine-readable code.

8. A cylindrical vessel with an identification label, the label comprising:

a first label portion with an underside coated with adhesive;

an opaque second label portion with a non-adhesive underside; and a transparent third label portion with an underside coated with adhesive; wherein a transition from a first outside edge of the first label portion and a second outside edge of the third label portion has a rounded line profile, and wherein the identification label is applied onto the cylindrical vessel so that the outside edge of the third label portion runs parallel to an axis of the cylindrical vessel.

9. The cylindrical vessel according to claim 8, wherein the identification label is applied onto the vessel and the third label portion overlaps the second label portion.

10. The cylindrical vessel according to claim 8, wherein the second label portion and the third label portion form a banner, which projects from the cylindrical vessel.

11. The cylindrical vessel according to claim 10, wherein the cylindrical vessel is a syringe body of an injection syringe.

* * * * *